(12) United States Patent
Tomikawa et al.

(10) Patent No.: US 12,733,819 B2
(45) Date of Patent: Sep. 15, 2026

(54) BIOLOGICAL INFORMATION INPUT SYSTEM AND BIOLOGICAL INFORMATION INPUT METHOD

(71) Applicant: PARAMOUNT BED CO., LTD., Tokyo (JP)

(72) Inventors: Jun Tomikawa, Tokyo (JP); Yoshitomo Nagamine, Tokyo (JP); Masashi Gotoh, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 361 days.

(21) Appl. No.: 18/223,421

(22) Filed: Jul. 18, 2023

(65) Prior Publication Data

US 2023/0360753 A1 Nov. 9, 2023

Related U.S. Application Data

(63) Continuation of application No. PCT/JP2022/009731, filed on Mar. 7, 2022.

(30) Foreign Application Priority Data

Mar. 15, 2021 (JP) ................................ 2021-041077

(51) Int. Cl.
*A61B 5/01* (2006.01)
*A61B 5/02* (2006.01)
(Continued)

(52) U.S. Cl.
CPC .................. *A61B 5/01* (2013.01); *A61B 5/02* (2013.01); *G16H 10/60* (2018.01); *G16H 40/63* (2018.01)

(58) Field of Classification Search
CPC ..... A61N 1/37211; A61B 5/0022; A61B 5/01; A61B 5/002
See application file for complete search history.

(56) References Cited

U.S. PATENT DOCUMENTS

2009/0063193 A1* 3/2009 Barton .................. G08B 21/02 340/539.11

FOREIGN PATENT DOCUMENTS

JP 2011-81837 A 4/2011
JP 2013-196334 A 9/2013
(Continued)

OTHER PUBLICATIONS

International Search Report for PCT/JP2022/009731 mailed on May 24, 2022.
(Continued)

*Primary Examiner* — Michael J D'Abreu
(74) *Attorney, Agent, or Firm* — Birch, Stewart, Kolasch & Birch, LLP

(57) ABSTRACT

A biological information input system includes: a measurement instrument having a communication function and configured to measure biological information of a person under measurement; and a first terminal device having a communication function capable of communicating with the communication function of the measurement instrument, and configured to receive, via the communication function, the biological information associated with the person under measurement and measured by the measurement instrument. The biological information input system displays a screen with which a person having authority to approve the biological information approves first data including the biological information and information related to the person under measurement.

4 Claims, 15 Drawing Sheets

(51) Int. Cl.
*G16H 10/60* (2018.01)
*G16H 40/63* (2018.01)

(56) References Cited

FOREIGN PATENT DOCUMENTS

| | | | |
|---|---|---|---|
| JP | 2019-121206 | A | 7/2019 |
| JP | 2020-160672 | A | 10/2020 |
| JP | 2020-187597 | A | 11/2020 |
| JP | 6793225 | B2 | 12/2020 |

OTHER PUBLICATIONS

Tomikawa, "Overview of IT systems centered on hospital beds and the benefits they bring to hospitals," New Medicine in Japan, vol. 46, No. 7, Jul. 1, 2019, pp. 90-93 (8 pages total), with English translation.

* cited by examiner

FIG. 4

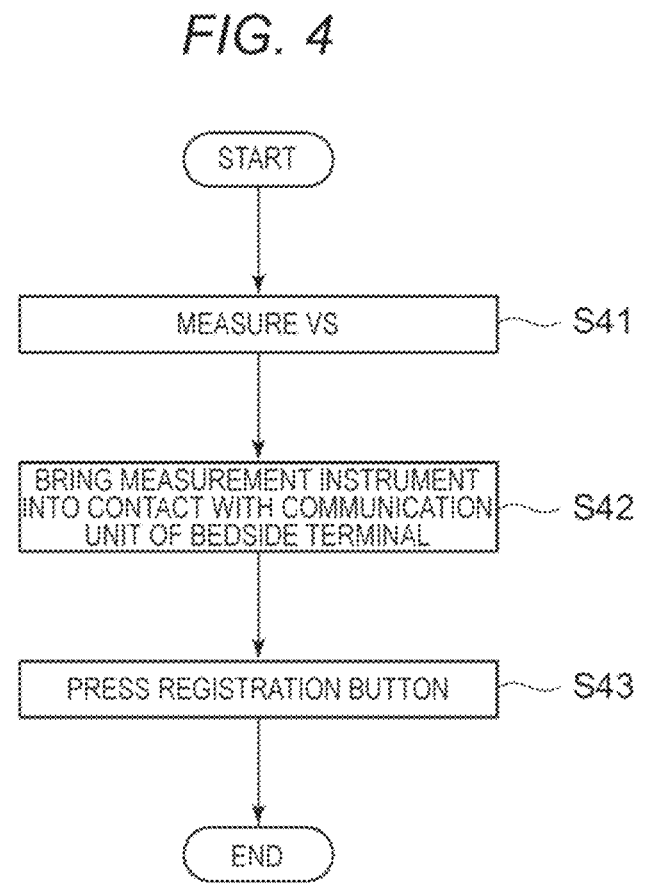

START

MEASURE VS — S41

BRING MEASUREMENT INSTRUMENT INTO CONTACT WITH COMMUNICATION UNIT OF BEDSIDE TERMINAL — S42

PRESS REGISTRATION BUTTON — S43

END

58
LOGIN
ERROR
NOTIFICATION
ONGOING
2022/09/20
301
301
301
301

59
310
310
2022/09/20
ERROR
NOTIFICATION
ONGOING
Mr
Ms

Figure 15:
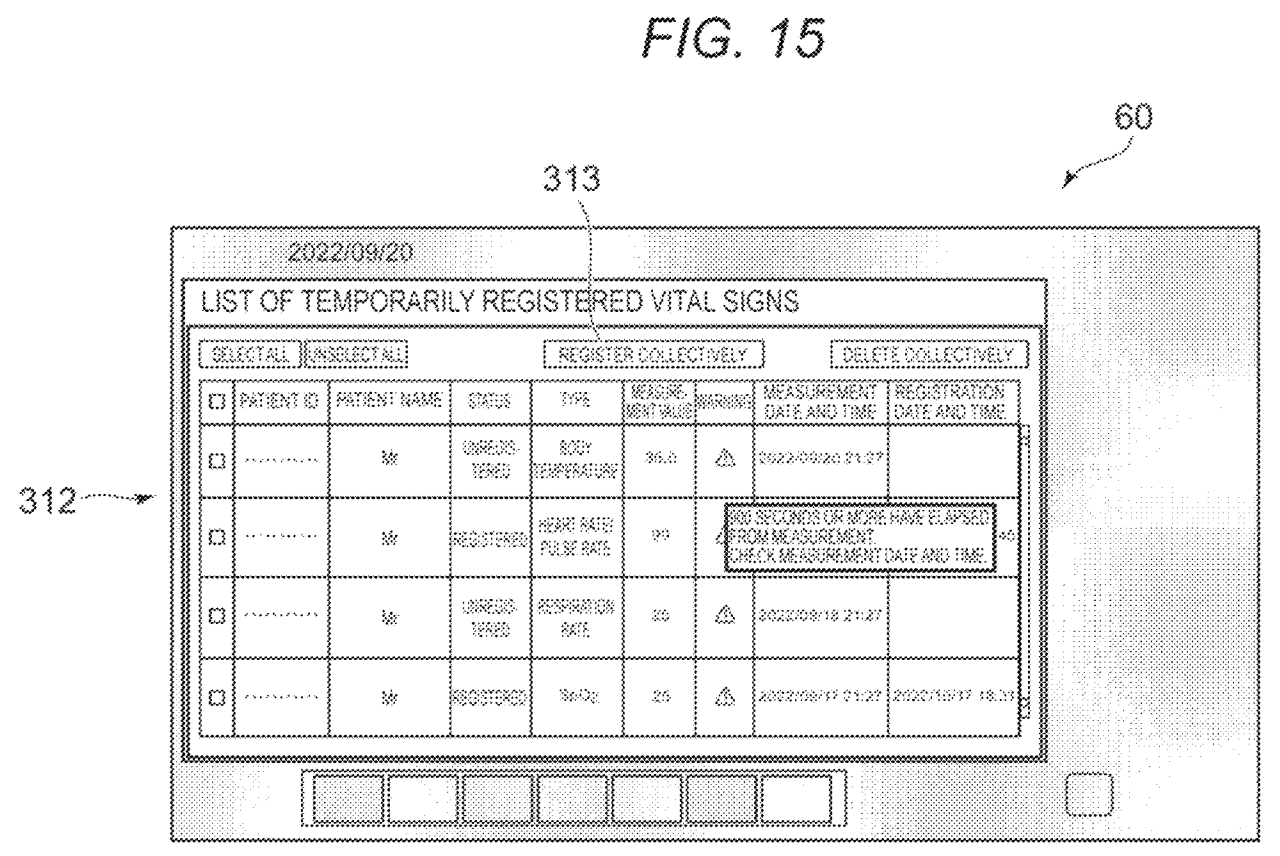

LIST OF TEMPORARILY REGISTERED VITAL SIGNS

SELECT ALL

UNSELECT ALL

REGISTER COLLECTIVELY

DELETE COLLECTIVELY

BIOLOGICAL INFORMATION INPUT SYSTEM AND BIOLOGICAL INFORMATION INPUT METHOD

CROSS REFERENCE TO RELATED APPLICATIONS

This application is a Continuation of PCT International Application No. PCT/JP2022/009731, filed on Mar. 7, 2022, which claims priority under 35 U.S.C. 119(a) to Patent Application No. 2021-041077, filed in Japan on Mar. 15, 2021, all of which are hereby expressly incorporated by reference into the present application.

FIELD

An embodiment relates to a biological information input system and a biological information input method.

BACKGROUND

In the related art, in medical facilities such as hospitals, biological information such as vital signs of a patient has been measured on a daily basis and input to an electronic medical record. In recent years, it also has been proposed to measure biological information of a patient by a measurement instrument equipped with a near field communication (NFC) function, transfer the biological information to a terminal device disposed on a bedside of the patient by the NFC, and register the biological information in an electronic medical record. However, since only a medical professional registered in advance is allowed to operate the terminal device that registers the biological information, the medical professional needs to go to a place of the patient every time the biological information is measured and registered.

In recent years, shortage of medical professionals has become a serious social problem. When the patient has an infectious disease, it is preferable to reduce an opportunity of contact with the patient even for the medical professional. Therefore, when the medical professional goes to the place of the patient only for the measurement and registration of the biological information, there is a possibility that a load on the medical professional is increased or infection is spread.

BRIEF DESCRIPTION OF THE DRAWINGS

FIG. 4 is a flowchart showing actions of a patient in the biological information input method according to the embodiment;

FIG. 15 is a diagram showing a screen displayed by the biological information input system according to the embodiment.

DETAIL DESCRIPTION

Figure 1:
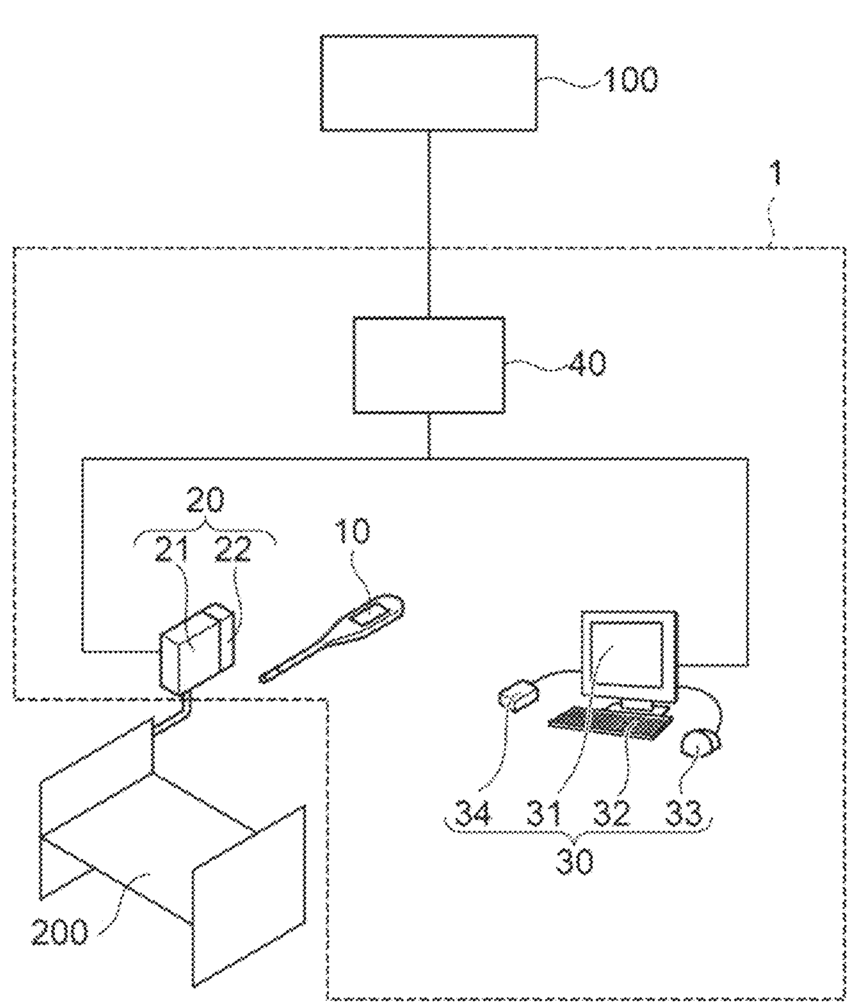
FIG. 1 is a diagram showing a biological information input system according to an embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, one aspect of the present application is a biological information input system including: a measurement instrument having a communication function and configured to measure biological information of a person under measurement; and a first terminal device having a communication function capable of communicating with the communication function of the measurement instrument, and configured to receive, via the communication function, the biological information associated with the person under measurement and measured by the measurement instrument. The biological information input system displays a screen with which a person having authority to approve the biological information approves first data including the biological information and information related to the person under measurement.

Another aspect of the present application is a biological information input method includes: measuring biological information of a person under measurement by a measurement instrument having a communication function; acquiring the biological information by the communication function and storing first data including the biological information and information related to the person under measurement; and displaying a screen with which a person having authority to approve the biological information approves the first data.

Hereinafter, one or more embodiments are described with reference to the drawings.

FIG. 1 is a diagram showing a biological information input system according to the present embodiment.

As shown in FIG. 1, a biological information input system 1 according to the present embodiment includes a measurement instrument 10, a bedside terminal 20 (first terminal device), a station terminal 30 (second terminal device), and a server 40.

In the present embodiment, the biological information input system 1 is constructed in a hospital. In the hospital, an electronic medical record 100 is constructed apart from the biological information input system 1. The electronic medical record 100 has authority to be operated only by a preregistered person, for example, a doctor and a nurse (hereinafter, collectively referred to as "medical professional") who work in the hospital. The electronic medical record 100 is a type of electronic medical system. In the present specification, the "electronic medical system" refers to a system that is electronically constructed, manages medical information, and has authority to be operated only by the preregistered person. On the other hand, a person who inputs biological information to the biological information input system 1 is not limited, and for example, a person under measurement can input the biological information by himself/herself. Meanwhile, a person having authority to approve information input to the biological information input system 1 is limited to the preregistered person, for example, the medical professional who works in the hospital.

The measurement instrument 10 is an instrument that measures biological information of a human body. The biological information is, for example, a vital sign value, and includes at least one parameter of a body temperature, a pulse rate, and a blood pressure. In addition, the biological information may include at least one parameter among a respiratory rate, an arterial blood oxygen saturation ($SPO_2$), and a blood glucose level. The biological information may include parameters other than those described above. The person under measurement can measure his/her own biological information by operating the measurement instrument 10. The person under measurement is, for example, an inpatient. The measurement instrument 10 has a communication function. The communication function is, for example, a short-distance communication function, for example, near field communication (NFC).

Hereinafter, in the present embodiment, the NFC will be described as an example of the communication function of the measurement instrument 10 and the bedside terminal 20. Since a communication distance of the NFC is about several mm to several cm, a transmission-side instrument and a reception-side instrument are preferably in contact with each other for the purpose of communication, but swiping may only be performed without the necessity of being in contact. In the present embodiment, a case of contact and a case of swiping are collectively referred to as "contact". A case of using a communication function other than the NFC will be described later.

The body temperature can be measured by, for example, a thermometer. In this case, the measurement instrument 10 is a thermometer with the short-distance communication function. The pulse rate and the blood pressure can be measured by, for example, a sphygmomanometer. In this case, the measurement instrument 10 is a sphygmomanometer with the short-distance communication function. The arterial blood oxygen saturation ($SPO_2$) can be measured by, for example, a pulse oximeter. In this case, the measurement instrument 10 is a pulse oximeter with the short-distance communication function. The blood glucose level can be measured by, for example, a blood glucose self-monitoring device. In this case, the measurement instrument 10 is a blood glucose self-monitoring device with the short-distance communication function.

The bedside terminal 20 is installed near a specific patient. For example, a certain patient occupies a specific bed 200, and the bedside terminal 20 is attached to the bed 200 or installed in the vicinity of the bed 200. The bedside terminal 20 is associated with the patient. For example, the bedside terminal 20 is associated with the patient using the number of an installation place of the bed 200. A method of associating the bedside terminal 20 with the patient is not limited to a method of using the number of the installation place of the bed 200, and may be, for example, a method of reading a barcode displayed on a wrist band of the patient with a bar code reader or a method of inputting an identity document (ID) of the patient.

The bedside terminal 20 includes, for example, a touch panel 21 and a communication unit 22. The touch panel 21 can display a screen for the patient and a screen for the medical professional, and receive information that are input via the respective screens. The communication unit 22 can electronically input the biological information measured by the measurement instrument 10 and a measurement time to the bedside terminal 20 by coming into contact with the measurement instrument 10. In addition, the communication unit 22 authenticates a medical professional by, for example, coming into contact with an ID card of the medical professional. The bedside terminal 20 may authenticate the medical professional by inputting the ID and password of the medical professional to the touch panel 21. In addition, a function of communicating with the measurement instrument 10 and a function of authenticating the medical professional in the communication unit 22 may be implemented by different hardware.

The station terminal 30 is installed at a location different from the bedside terminal 20, for example, a staff station of the hospital. The staff station is, for example, a nurse station. The station terminal 30 is not operated by the patient.

The station terminal 30 is provided with, for example, a display 31, a keyboard 32, a mouse 33, and an authentication unit 34. The authentication unit 34 authenticates a medical professional by, for example, coming into contact with an ID card of the medical professional. The station terminal 30 may authenticate the medical professional by inputting the ID and password of the medical professional by the keyboard 32.

The server 40 is connected to the bedside terminal 20 and the station terminal 30. The bedside terminal 20, the station terminal 30, and the server 40 frequently exchange data with each other. The server 40 is connectable to the electronic medical record 100.

When the biological information and the measurement time are input from the measurement instrument 10 via the bedside terminal 20, the biological information input system 1 generates first data by adding, to the biological information and the measurement time, information related to the patient and a time at which the biological information is transferred from the measurement instrument 10 to the bedside terminal 20. The first data is stored in, for example, the server 40.

The biological information input system 1 can display the first data on the bedside terminal 20 and the station terminal 30 in response to a request from a medical professional. The medical professional can approve the first data via the bedside terminal 20 and can also approve the first data via the station terminal 30.

Before a medical professional, that is, a person having authority to approve the first data, approves the first data, the biological information input system 1 identifies and holds the first data as a "temporary registration state". When the medical professional approves the first data, the biological information input system 1 creates second data by adding information of the medical professional who approves the first data to the first data, and stores the second data in the server 40. In practice, the server 40 may identify the biological information or the like stored as the first data as a "formal registration state" and set the biological information or the like as a part of the second data. Then, the server 40 outputs the formally registered second data to the electronic medical record 100.

Next, operation of the above biological information input system, that is, a biological information input method according to the present embodiment will be described.

Figure 2:
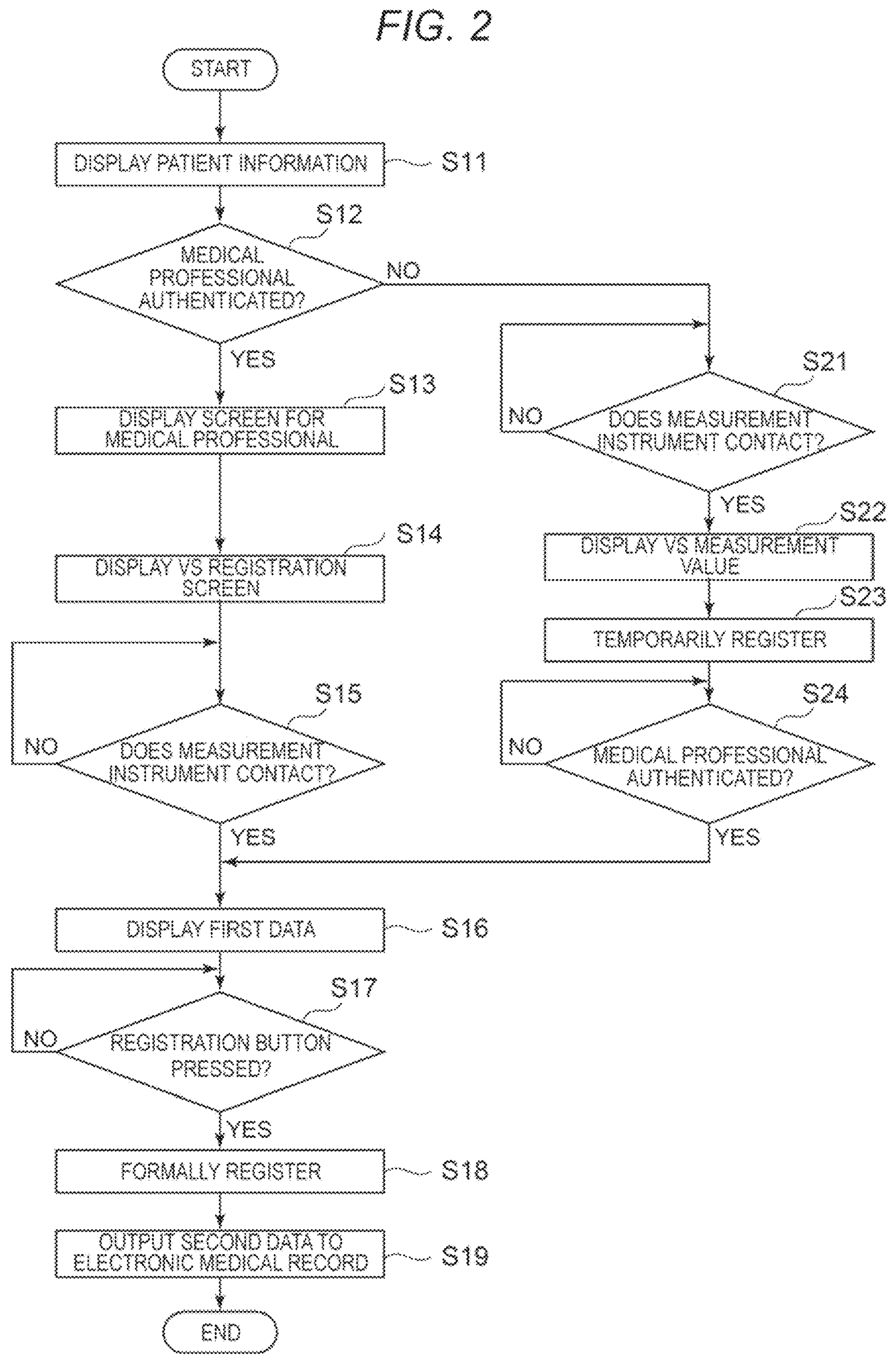
FIG. 2 is a flowchart showing a biological information input method according to the embodiment.

FIG. 2 is a flowchart showing the biological information input method according to the present embodiment.

Figure 3:
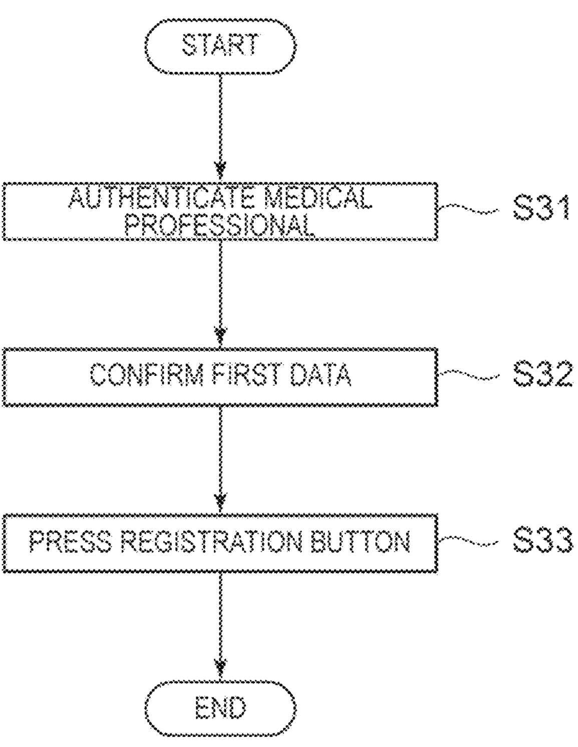
FIG. 3 is a flowchart showing actions of a medical professional in the biological information input method according to the embodiment.

FIG. 3 is a flowchart showing actions of a medical professional in the biological information input method according to the present embodiment.

FIG. 4 is a flowchart showing actions of a patient in the biological information input method according to the present embodiment.

FIGS. 5 to 15 are diagrams showing screens displayed by the biological information input system according to the present embodiment.

In FIGS. 2 to 4, the biological information is expressed as a "vital sign" (VS). The screens shown in FIGS. 5 to 15 are examples, and a layout of each screen is optional.

First, a situation as a premise of the biological information input method according to the present embodiment will be described.

Figure 5:
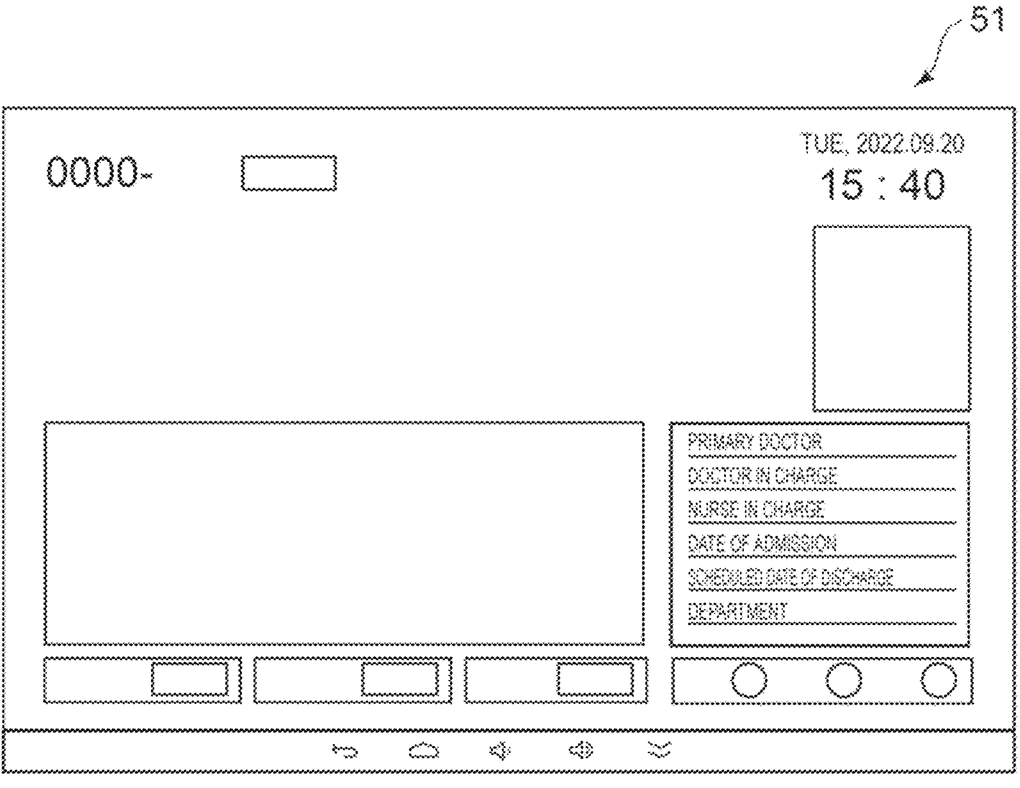
FIG. 5 is a diagram showing a screen displayed by the biological information input system according to the embodiment.
Figure 6:
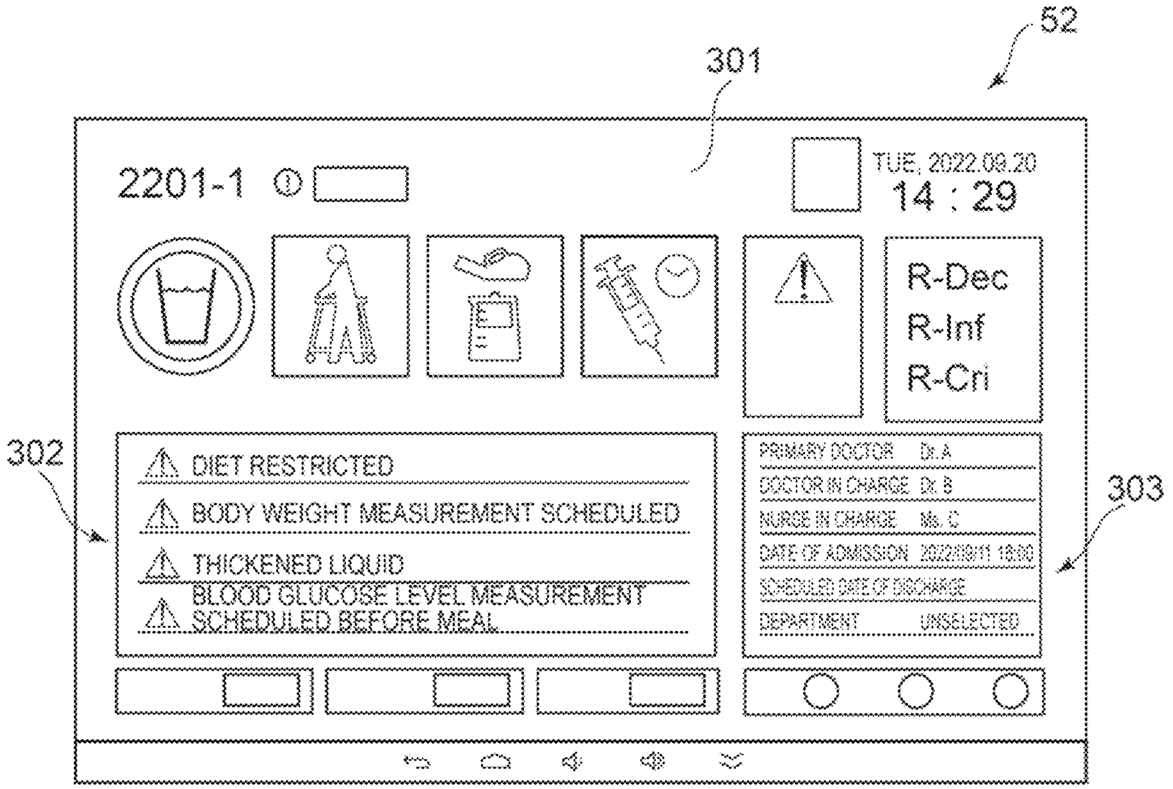
FIG. 6 is a diagram showing a screen displayed by the biological information input system according to the embodiment.
Figure 7:
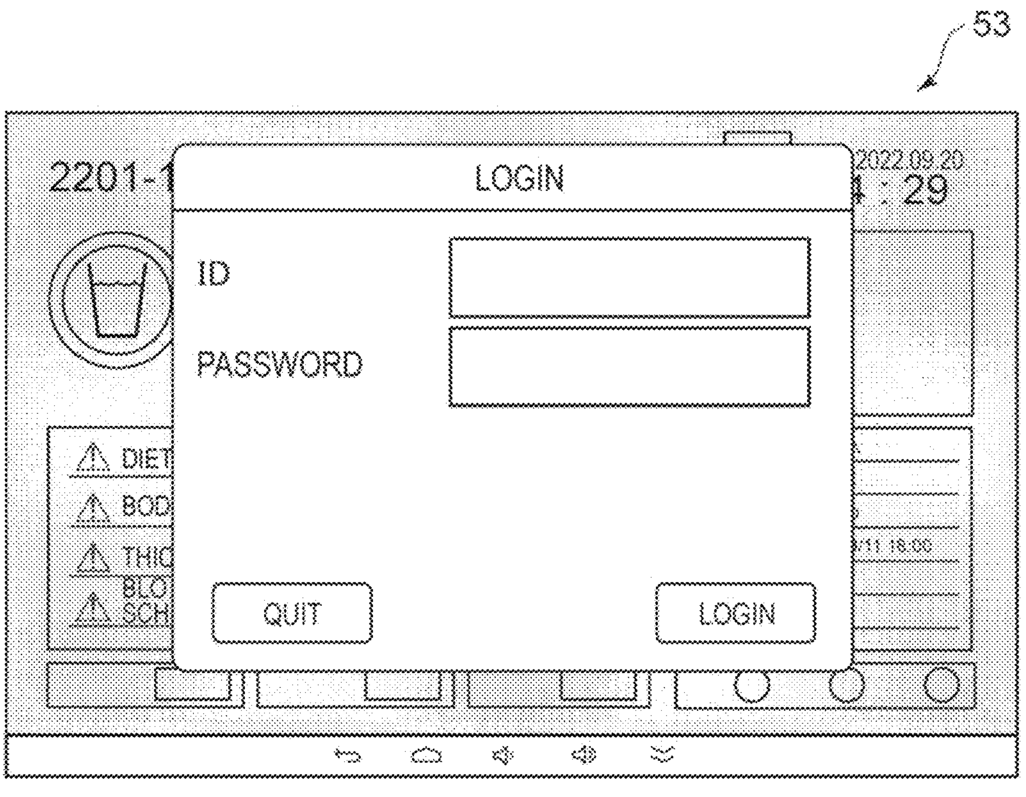
FIG. 7 is a diagram showing a screen displayed by the biological information input system according to the embodiment.
Figure 8:
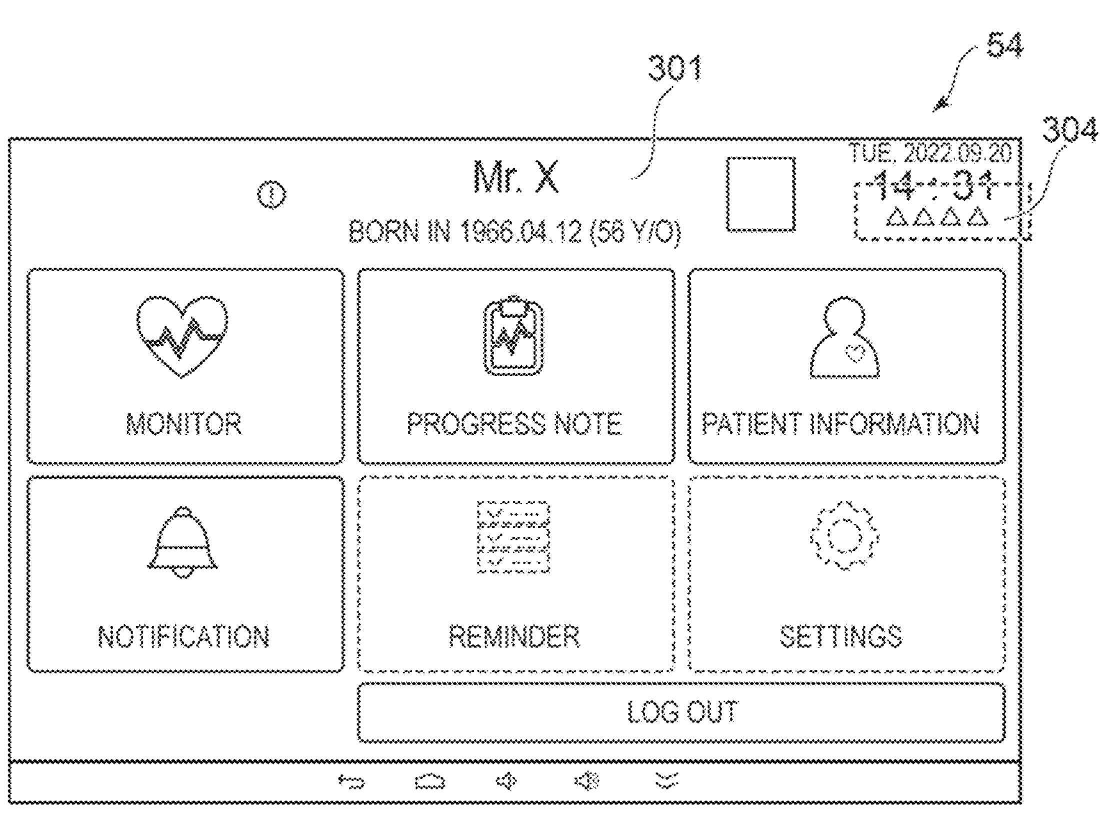
FIG. 8 is a diagram showing a screen displayed by the biological information input system according to the embodiment.

A patient who is a person under measurement stays in a hospital and is present on the specific bed 200 installed in a specific ward. The bedside terminal 20 is disposed in the vicinity of the bed 200. The measurement instrument 10 is placed in the vicinity of the bed 200. The server 40 stores information of the patient and the medical professional. The server 40 associates the information of the patient with the bedside terminal 20. When the patient is not associated with the bedside terminal 20, a blank screen 51 as shown in FIG. 5 is displayed on the touch panel 21.

Next, a case where a medical professional is in a ward will be described.

As shown in step S11 of FIGS. 1 and 2, in the biological information input system 1 (hereinafter, simply referred to as "system 1"), the bedside terminal 20 displays information on a patient associated with the bedside terminal 20 on the touch panel 21. For example, the bedside terminal 20 displays a screen 52 shown in FIG. 6. The screen 52 displays a name 301 of a patient, medical information 302 related to the patient, information 303 related to the medical professional in charge of the patient, and the like.

As shown in step S31 of FIG. 3, the medical professional brings his/her own ID card into contact with the communication unit 22 of the bedside terminal 20 to perform medical professional authentication. Accordingly, the medical professional can operate the bedside terminal 20 as the medical professional. The medical professional may perform the medical professional authentication by displaying a log-in screen 53 shown in FIG. 7 on the touch panel 21 and inputting his/her own ID and password on the log-in screen 53 without using the communication unit 22.

The system 1 proceeds to step S13 through step S12 in FIG. 2, and displays a screen for a medical professional. For example, as in a screen 54 shown in FIG. 8, the screen for medical professional indicates a name 304 of the authenticated medical professional in addition to information related to the patient.

Figure 9:
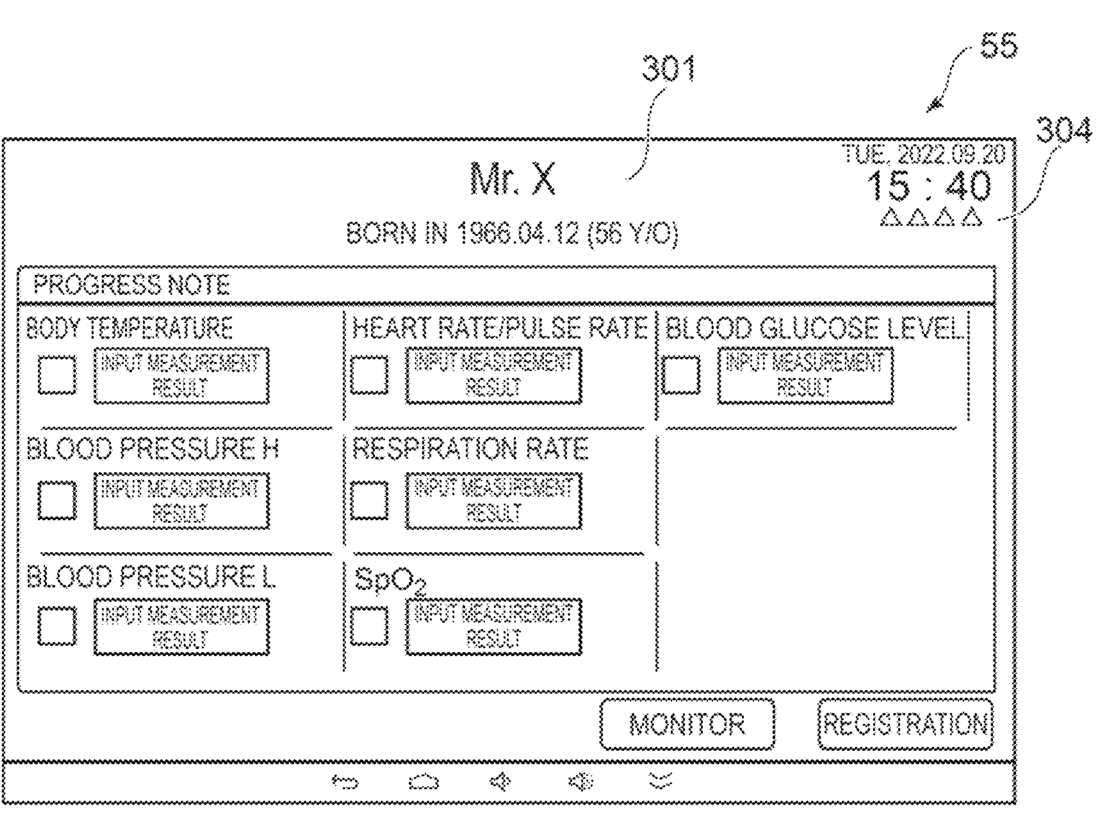
FIG. 9 is a diagram showing a screen displayed by the biological information input system according to the embodiment.

Next, the system 1 proceeds to step S14 and displays a screen 55 for registering biological information shown in FIG. 9. Parameters of the biological information to be input are displayed on the screen 55.

Next, the medical professional or the patient measures the biological information of the patient using the measurement instrument 10. Then, the medical professional or the patient brings the measurement instrument 10 into contact with the communication unit 22 of the bedside terminal 20. Accordingly, the measured biological information and the measurement time of the biological information are input from the measurement instrument 10 to the bedside terminal 20. The screen 54 may be switched to the screen 55 by bringing the measurement instrument 10 into contact with the communication unit 22 in a state where the screen 54 is displayed.

The system 1 proceeds from step S15 to step S16 in FIG. 2, creates the first data including a measurement value of the biological information, the measurement time of the biological information, a transfer time of the biological information, and information related to the patient, and displays the first data on the touch panel 21 of the bedside terminal 20. For example, the bedside terminal 20 displays a screen 56 shown in FIG. 10. The screen 56 displays the first data, that is, measured biological information 305, a measurement time 306, and the name 301 of the patient. A "registration" button 307 is also displayed on the screen 56.

Figure 10:
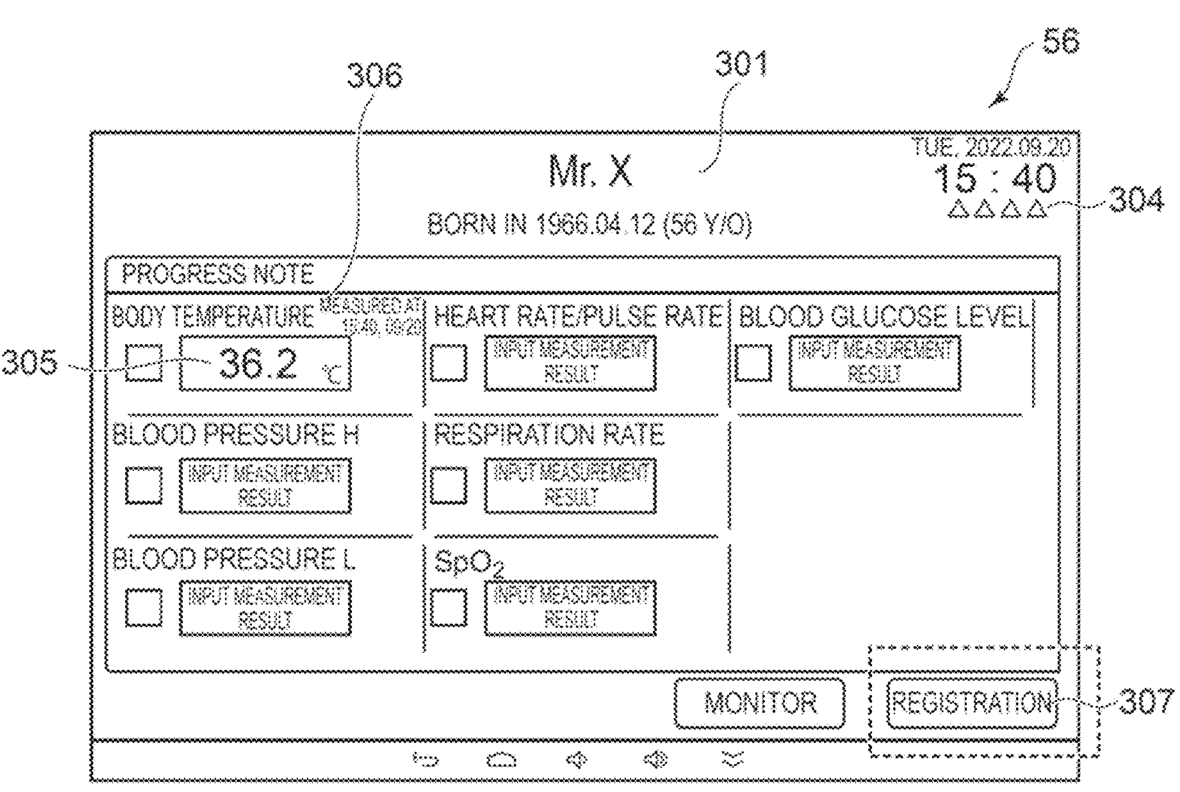
FIG. 10 is a diagram showing a screen displayed by the biological information input system according to the embodiment.

As shown in step S32 of FIG. 3, the medical professional confirms the first data displayed on the screen 56 (FIG. 10). When there is no problem, the "registration" button 307 is pressed as shown in step S33. The medical professional can modify content of the biological information 305 or the measurement time 306 and then press the "registration" button 307. In this case, the modified first data is registered.

The "time" included in the first data may include three types of times. The three types of time are the measurement time 306 of the biological information stored in the measurement instrument 10, a time when the medical professional presses the "registration" button 307, and an input time when the medical professional inputs a time after the "registration" button is pressed.

The system 1 proceeds from step S17 to step S18 in FIG. 2, creates the second data by adding information related to a medical professional who registers the first data to the first data, and stores the second data in the server 40. At this time, a code representing "formal registration" is added to the second data. Alternatively, the second data is stored in a data table different from the first data.

Next, as shown in step S19 of FIG. 2, the system 1 outputs the second data stored in the server 40 and identified as "formal registration" to the electronic medical record 100. Accordingly, the input of the biological information is completed.

Next, a case where the medical professional is not in the ward will be described.

As shown in step S11 of FIG. 2, the system 1 displays the screen 52 (FIG. 6) on the touch panel 21 of the bedside terminal 20.

As shown in step S41 of FIGS. 1 and 4, the patient measures his/her own biological information using the measurement instrument 10 when a predetermined time comes or when the patient is remotely instructed by the medical professional.

Next, as shown in step S42 of FIGS. 1 and 4, the patient brings the measurement instrument 10 into contact with the communication unit 22 of the bedside terminal 20. Accordingly, the measured biological information and the measurement time of the biological information are electronically input from the measurement instrument 10 to the bedside terminal 20.

Figure 11:
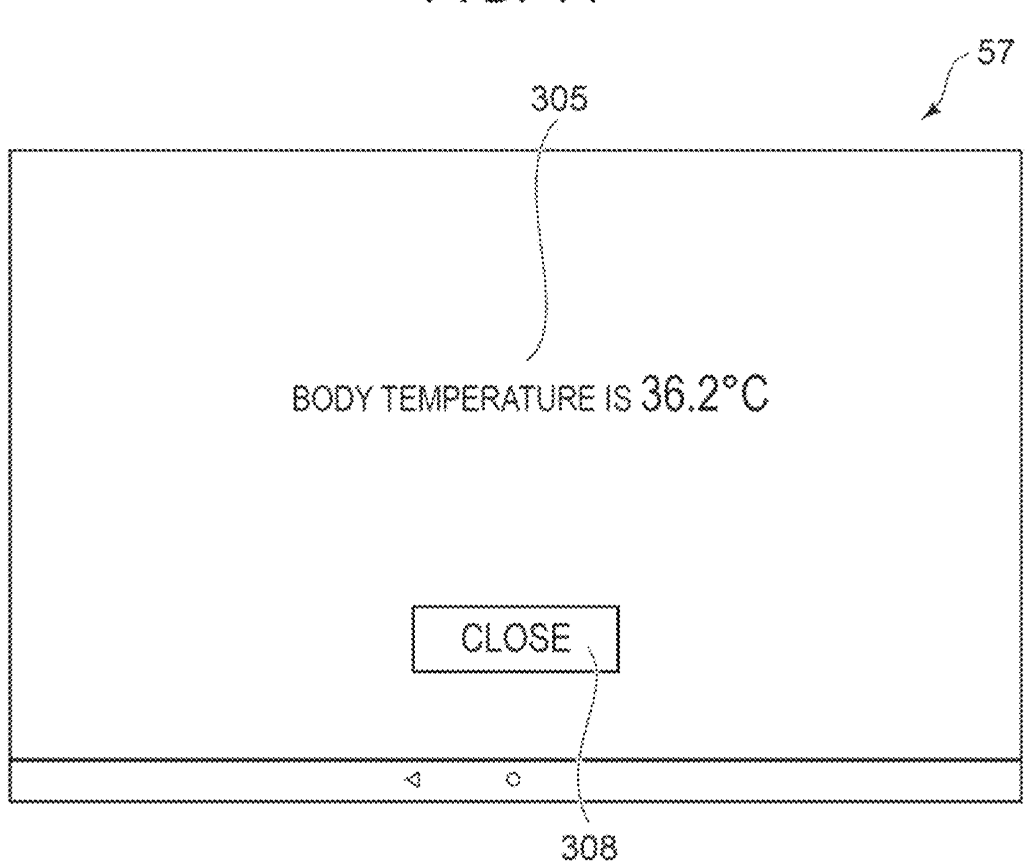
FIG. 11 is a diagram showing a screen displayed by the biological information input system according to the embodiment.
Figure 12:
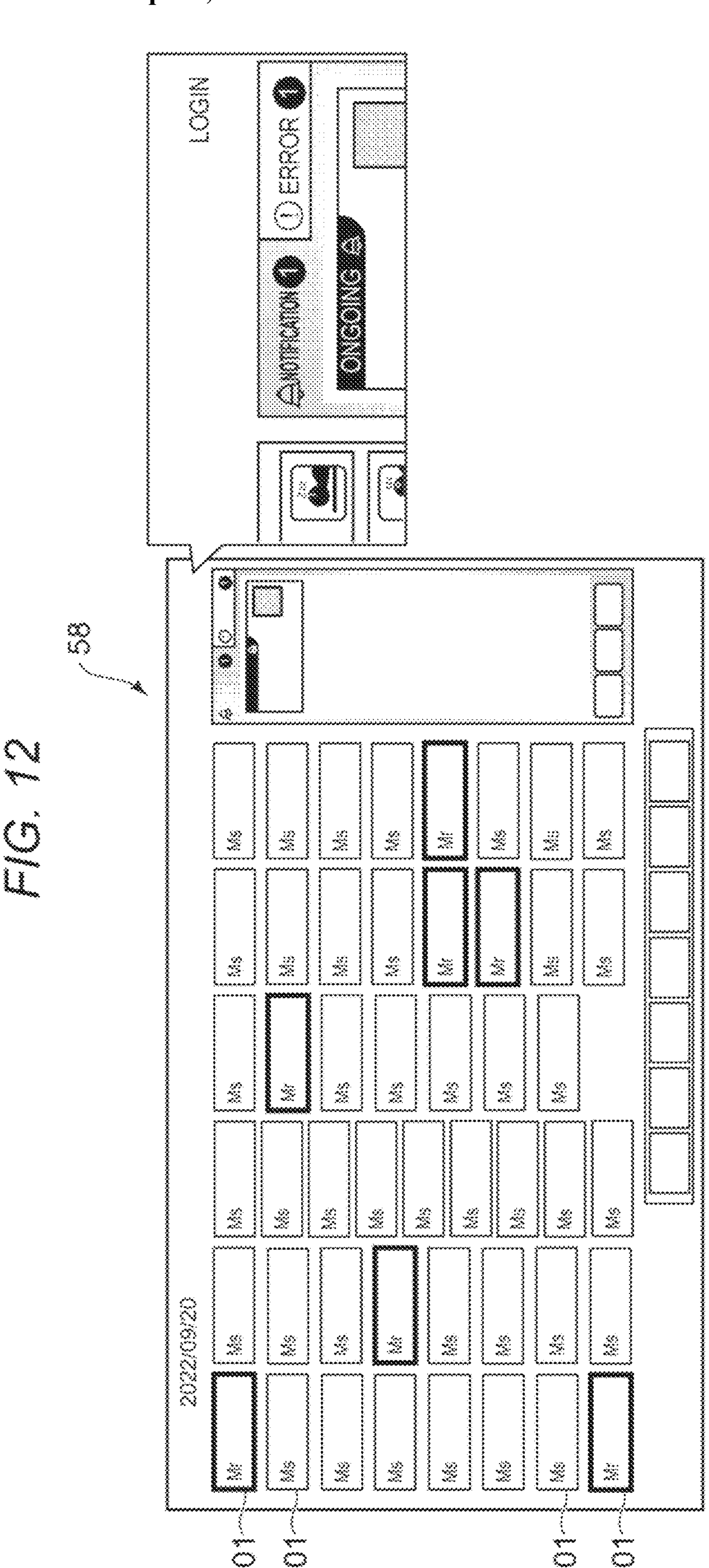
FIG. 12 is a diagram showing a screen displayed by the biological information input system according to the embodiment.

At this time, since the bedside terminal 20 has not been subjected to the medical professional authentication, the system 1 proceeds from step S11 to step S21 through step S12. Then, since the measurement instrument 10 comes into contact with the communication unit 22 of the bedside terminal 20, the system 1 proceeds to step S22 and displays the measurement value of the biological information 305 on the touch panel 21. For example, the touch panel 21 displays a screen 57 (FIG. 11). On the screen 57, a "registration" button is not displayed, and a "close" button 308 is displayed.

As shown in step S43 of FIG. 4, the patient confirms the measurement value of the biological information on the screen 57. After the confirmation, when the patient presses the "close" button 308 or a prescribed time elapses, a screen of the bedside terminal 20 returns to the screen 52 (see FIG. 6) indicating the patient information. Processes to be performed by the patient are now completed. The patient is not permitted to modify the measurement value of the biological information.

As shown in step S23 of FIG. 2, the system 1 creates the first data including the measurement value of the biological information, the measurement time of the biological information, the transfer time of the biological information, and the information related to the patient, and stores the first data in the server 40. At this time, the system 1 adds a code representing "temporary registration" to the first data. Alternatively, the first data is stored in a data table of "temporary registration".

Meanwhile, the station terminal 30 displays a screen 58 (FIG. 12) on the display 31. Names 301 of a plurality of patients are displayed on the screen 58. The names 301 of the patients whose biological information is in the temporary registration state may be emphasized by, for example, a method of surrounding the names with a thick frame.

Figure 13:
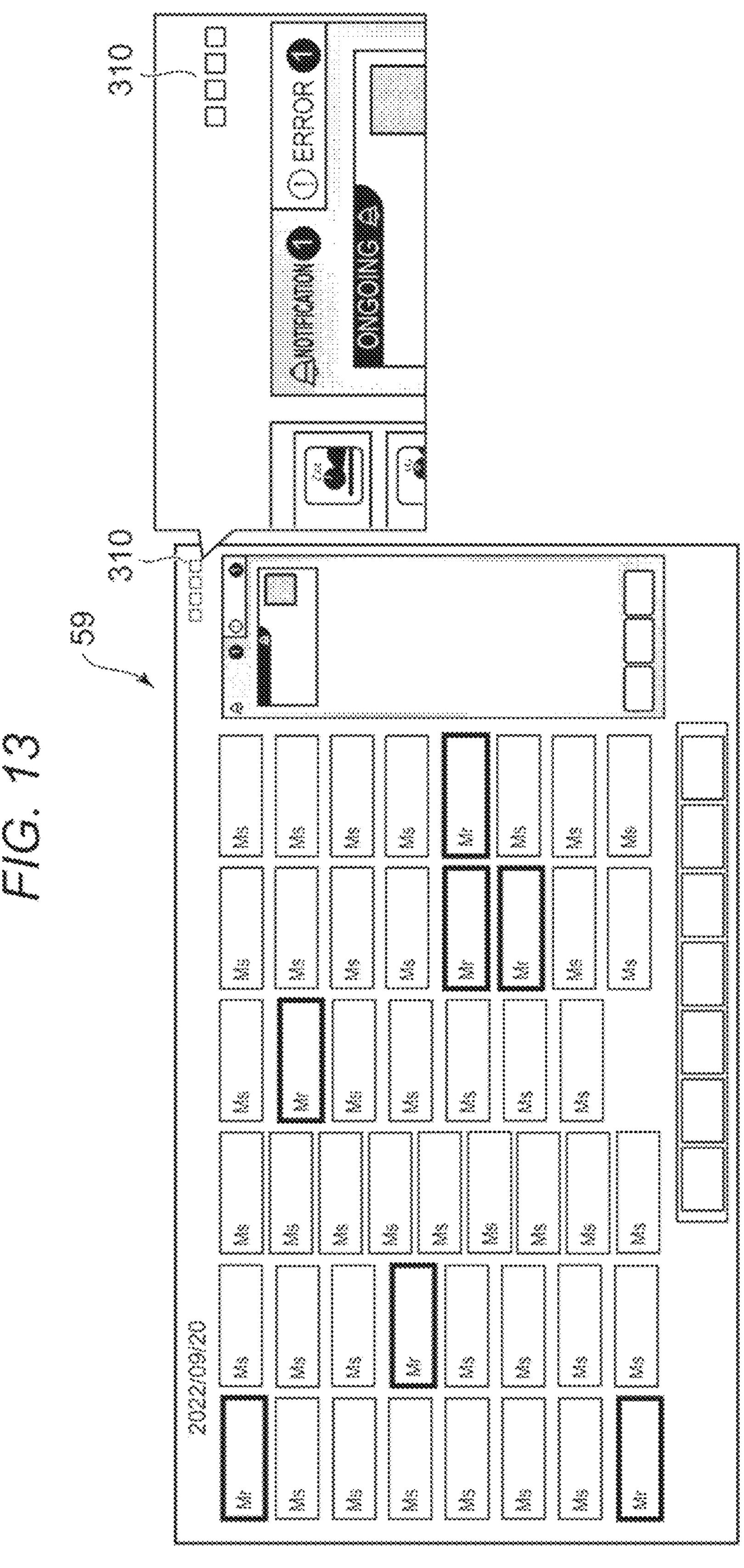
FIG. 13 is a diagram showing a screen displayed by the biological information input system according to the embodiment.

As shown in step S31 of FIG. 3, the medical professional brings the ID card into contact with the authentication unit 34 of the station terminal 30 to perform the medical professional authentication. Accordingly, the medical professional can operate the station terminal 30. At this time, the medical professional authentication may be performed by displaying the log-in screen 53 (FIG. 7) on the station terminal 30 and inputting his/her own ID and password of the medical professional. When the medical professional is authenticated, the station terminal 30 displays a screen 59 (FIG. 13). The screen 59 displays a name 310 of the authenticated medical professional.

Figure 14:
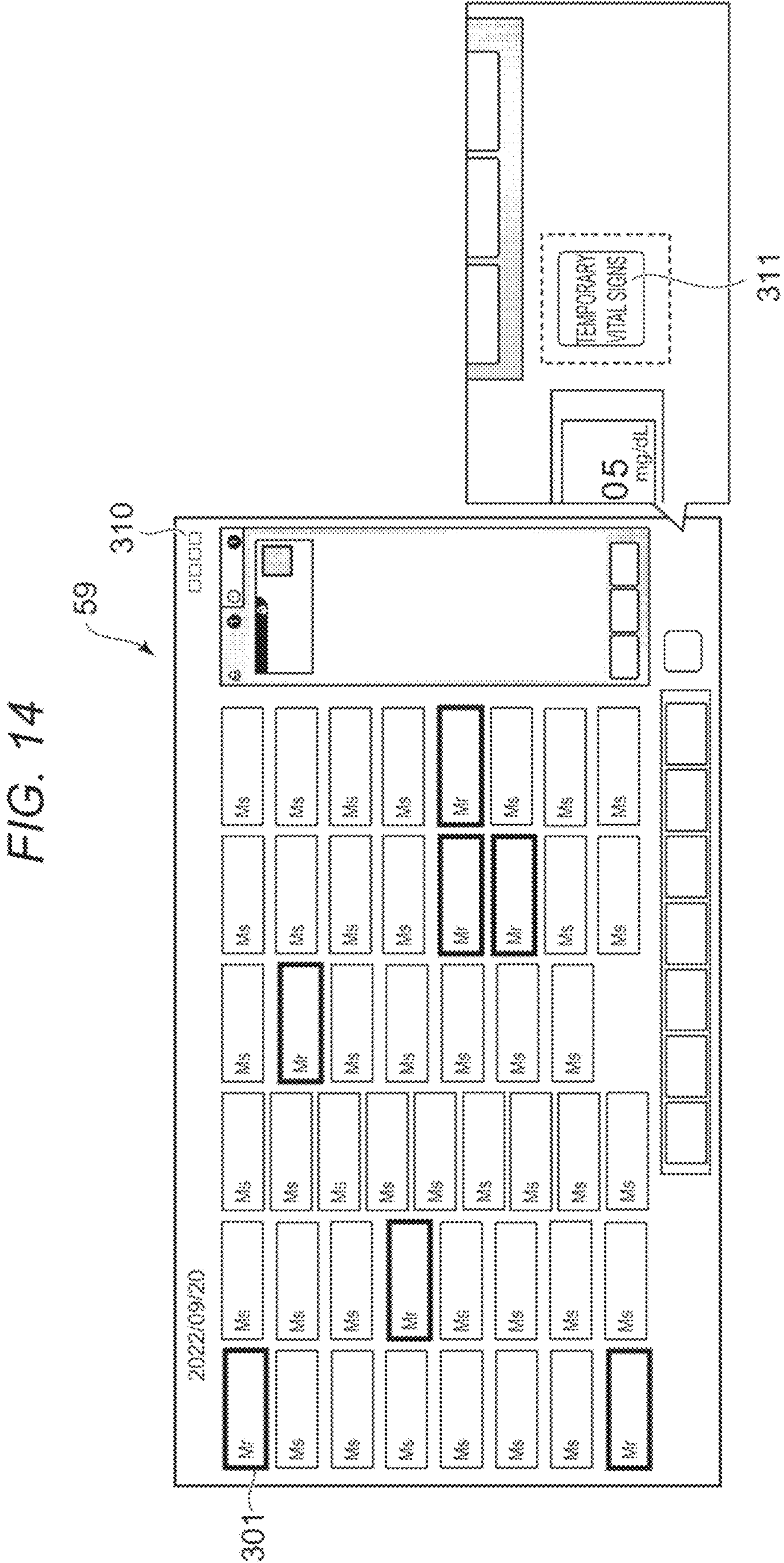
FIG. 14 is a diagram showing a screen displayed by the biological information input system according to the embodiment.

As shown in FIG. 14, when the medical professional selects a specific patient from the screen 59 and presses a button 311 that confirms temporary registration, the system 1 proceeds from step S24 to step S16, and displays a screen 60 shown in FIG. 15 on the display 31 of the station terminal 30. On the screen 60, first data 312 including biological information measured by the patient is displayed. A "registration" button 313 is also displayed on the screen 60.

At this time, when the first data is abnormal, the system 1 can display the abnormality on the station terminal 30. For example, when there is a certain time difference or more between a time when the measurement instrument 10 measures biological information and a time when data is transferred from the measurement instrument 10 to the bedside terminal 20, the system 1 may display a warning on the station terminal 30. In this case, the bedside terminal 20 does not display the warning.

As shown in step S32 of FIG. 3, the medical professional confirms the first data 312 displayed on the display 31. When there is no problem, the "registration" button 313 is pressed as shown in step S33. As described above, the medical professional can modify contents of the first data 312 and then press the "registration" button.

When the "registration" button 313 is pressed, the system 1 proceeds from step S17 to step S18 in FIG. 2, creates the second data by adding the information related to the medical professional to the first data, and stores the second data in the server 40. At this time, a code representing "formal registration" is added to the stored second data. Alternatively, the second data is stored in a data table of the "formal registration".

Next, as shown in step S19 of FIG. 2, the system 1 outputs the stored second data to the electronic medical record 100. Accordingly, the input of the biological information is completed.

Operation of the medical professional shown in steps S31 to S33 of FIG. 3 may be performed via the bedside terminal 20. For example, the operation shown in steps S31 to S33 may be performed when the medical professional visits a patient for a medical practice other than measurement of the biological information.

Next, effects of the present embodiment will be described.

According to the present embodiment, the patient can measure the biological information by himself/herself. At this time, since information is transmitted from the measurement instrument 10 to the bedside terminal 20 by the communication function, it is possible to prevent erroneous input compared to a case where the patient manually inputs a value of the biological information. In addition, the medical professional confirms information such as temporarily registered biological information and then approves these information to thereby formally register these information, and the formally registered information is output to the electronic medical record 100. Therefore, reliability of the information input to the electronic medical record 100 can be ensured.

In addition, according to the present embodiment, timing at which the patient measures the biological information and timing at which the medical professional approves the measured biological information and performs the formal registration can be temporally independent. In addition, the medical professional can approve the biological information temporarily registered for a plurality of patients at the same timing via the station terminal 30. Accordingly, the medical professional is not constrained by the measurement time of the biological information, and a degree of freedom of the actions of the medical professional is improved. Accordingly, a load on the medical professional can be reduced.

Furthermore, according to the present embodiment, the medical professional doesn't need to visit the patient only for measuring the biological information. Accordingly, the load on the medical professional is reduced. In addition, when the patient has an infectious disease, a risk of infection can be reduced.

In the present embodiment, an example in which the communication function is the NFC is shown, but the present embodiment is not limited thereto. For example, the communication function may be wired communication. In this case, the measurement value or the like of the biological information can be transferred by connecting the measurement instrument 10 to the bedside terminal 20 by wire. In addition, the communication function may be wireless communication with a communication distance of about 10 m to 100 m, such as Bluetooth (registered trademark). In this case, the patient can measure the biological information while lying on the bed 200 and transfer a result to the bedside terminal 20 installed in the same ward. However, in this case, it is preferable that the measurement instrument 10 is associated with a patient one-to-one so as not to confuse the biological information with biological information of the other patients in the same ward or a close ward, and the measurement instrument 10 and the bedside terminal 20 are paired.

In the biological information input system according to the present embodiment, in addition to the bedside terminal 20 and the station terminal 30, or instead of the station terminal 30, a mobile terminal may be provided. The mobile terminal is possessed by the medical professional, the medical professional may use the mobile terminal to approve the temporarily registered biological information or the like. Accordingly, the medical professional can perform an approval process even if the medical professional is not at the staff station, and is further released from constraint of a location. In addition, the medical professional may approve the first data using the server 40.

The present embodiment shows an example in which the station terminal 30 and the server 40 are implemented by different hardware, but the station terminal 30 and the server 40 may be implemented by single hardware. For example, one of the plurality of station terminals 30 may have a server function. Alternatively, for example, in a small hospital, only one computer serving as a station terminal and a server may be provided. Alternatively, the bedside terminal 20, the station terminal 30, and the server 40 may be implemented by one computer.

The present embodiment shows an example in which a person under measurement related to biological information is an inpatient, but the present embodiment is not limited thereto. For example, the person under measurement may be an outpatient. In this case, the bedside terminal 20 may be installed in the patient's home, and may be connected to the server 40 installed in a hospital via a virtual private network (VPN) or the like.

In addition, the person under measurement may be a care receiver living in a care facility. In this case, the electronic medical system may be a care support system or a care record system constructed in the care facility. A person having authority to operate the electronic medical system is, for example, a caregiver who works in the care facility. In addition, a person having authority to approve biological information or the like in the system 1 is also, for example, a caregiver who works in the care facility.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A biological information input system comprising:

a measurement instrument having a communication function and configured to be associated with a patient, the measurement instrument configured to measure biological information of the associated patient; and a first terminal device comprising a communication unit and a first screen, the first terminal device configured to pair with the measurement instrument to receive, via the communication function, the measured biological information of the associated patient, wherein the first screen is configured to display information of the associated patient on the first screen;

a server configured to receive and store the measured biological information, measurement time, and information related to the patient as a first data in a temporary registration state, from the first terminal device; and a second terminal device, in communication with the first terminal device and server, the second terminal device including a second screen, wherein the second terminal device further configured to authenticate a medical professional having authority to approve the first data, wherein the second terminal device is configured to display, via the second screen, a name of the authenticated medical professional and a plurality of patients, and further display the first data of the associated patient, in response to the authenticated medical professional selecting the associated patient from the plurality of patients displayed, wherein the second terminal device is configured to create and store a second data on the server by adding information related to the authenticated medical professional and a code representing formal registration to the first data, in response to receiving an input indicating approval of the first data, from the authenticated medical professional, and wherein the system outputs the second data to an electronic medical record.

2. The biological information input system according to claim 1, wherein the first terminal device is installed in a ward of the associated patient, and the second terminal device is installed in a staff station.

3. The biological information input system according to claim 1, wherein the first terminal device is installed in a ward of the associated patient, and the second terminal device is a mobile terminal held by the authenticated medical professional.

4. A biological information input method comprising:

measuring, by a measurement instrument associated with a patient, biological information of the associated patient, the measurement instrument having a communication function;

acquiring, by a first terminal device via the communication function of the measurement instrument, the biological information by the communication function;

displaying, by the first terminal device, the biological information on a screen of the first terminal device;

receiving and storing, by a server in communication with the first terminal device, first data including the biological information and information related to the associated patient in a temporary registration state;

authenticating, at a second terminal device in communication with the first terminal device, a medical professional having authority to approve the first data;

displaying, on a screen of the second terminal device, a name of the authenticated medical professional and a plurality of patients, and display the first data of the associated patient, in response to the authenticated medical professional selecting the associated patient from the plurality of patients displayed;

creating and storing a second data on the server by adding information related to the authenticated medical professional and a code representing formal registration to the first data, in response to receiving an input indicating approval of the first data, from the authenticated medical professional; and outputting, by a system including the first terminal device, the second terminal device, and the server, the second data to an electronic medical record.

* * * * *